(12) United States Patent
Garti et al.

(10) Patent No.: US 7,182,950 B2
(45) Date of Patent: Feb. 27, 2007

(54) NANO-SIZED SELF-ASSEMBLED LIQUID DILUTABLE VEHICLES

(75) Inventors: Nissim Garti, Jerusalem (IL); Abraham Aserin, Jerusalem (IL); Aviram Spernath, Kfar Saba (IL); Idit Amar, Jerusalem (IL)

(73) Assignee: Nutralease Ltd., Ashkelon (IL)

( * ) Notice: Subject to any disclaimer, the term of this patent is extended or adjusted under 35 U.S.C. 154(b) by 18 days.

(21) Appl. No.: 10/173,508

(22) Filed: Jun. 12, 2002

(65) Prior Publication Data

US 2003/0232095 A1 Dec. 18, 2003

(51) Int. Cl.
*A01N 25/08* (2006.01)

(52) U.S. Cl. .......................... 424/401; 424/725; 516/20

(58) Field of Classification Search .................. 516/20; 424/401, 725
See application file for complete search history.

(56) References Cited

U.S. PATENT DOCUMENTS

| | | | |
|---|---|---|---|
| 5,536,504 A | | 7/1996 | Eugster et al. |
| 5,725,802 A | * | 3/1998 | Chittofrati et al. ............ 516/22 |
| 5,725,803 A | | 3/1998 | Engel |
| 6,048,846 A | * | 4/2000 | Cochran |
| 6,057,359 A | | 5/2000 | Eugster |
| 6,063,762 A | | 5/2000 | Hong et al. |
| 6,180,661 B1 | | 1/2001 | Eugster et al. |
| 6,248,363 B1 | | 6/2001 | Patel et al. |

FOREIGN PATENT DOCUMENTS

| | | |
|---|---|---|
| EP | 1 010 416 B1 | 4/2001 |
| GB | 588298 | 5/1947 |
| WO | WO 99/06043 | 2/1999 |
| WO | 9939715 | 8/1999 |
| WO | 9953925 | 10/1999 |
| WO | WO 01/37808 A1 | 5/2001 |
| WO | WO 02/09764 A1 | 2/2002 |

OTHER PUBLICATIONS

Garti et al. (J. Agric. Food Chem. (2001) vol. 49, pp. 2552-2562—published on the internet on Apr. 27, 2001).*
Solans, C., Pons, R., Kunieda, H., "Overview of Basic Aspects of Microemulsions" *Industrial Applications of Microemulsions*, Solans, C., Kunieda, H., Eds.; Dekker: New York, (1997); 66: 1-17.
Dungan, S.R., "Microemulsions in foods; properties and applications" *ibid*, 148-170.
Holmberg, K., "Quarter century progress and new horizons in microemulsions" in *Micelles, Microemulsions and Monolayers*, Shah, O., Ed.; Dekker: New York (1998) 161-192.
Garti, N., "Microemulsions, emulsions, double emulsions and emulsifiers in food" in *Formulation Science* (proceeding from Formulation forum '97—association of formulation chemists) (1998) I, 147-219.
Ezrahi, S., Aserin, A., Garti, N., "*Aggregation behavior in one-phase (Winsor IV) Microemulsions Systems*" in Microemulsions-fundamental and applied aspects Kumar, P., and Mittal, K.L., Eds. Marcel Dekker, Inc., New York (1999); 185-246.
Garti, N., Clement, V., Leser, M., Aserin, A., Fanun, M., "Sucrose ester Microemulsions" J. Molec. Liquids (1999) 80, 253-296.

* cited by examiner

*Primary Examiner*—Susan Coe Hoffman
(74) *Attorney, Agent, or Firm*—Greer, Burns & Crain Ltd.

(57) ABSTRACT

The present invention relates to nano-sized self-assembled structured concentrates and their use as effective suitable carriers for transferring active components into the human body. The nano-sized self-assembled concentrates are composed of an aqueous phase, an oil phase, a surfactant a co-solvent and co-surfactant. The formed nano-sized self-assembled structured concentrates may be in the form of an aqueous continuous phase, an oil continuous phase or a bicontinuous phase, and may thus be diluted to any desired extent in either oil or water maintaining their structure and the active material comprised within the nano-sized self-assembled structured concentrates.

20 Claims, 11 Drawing Sheets

Solubilization Efficacy of Phytosterols

NANO-SIZED SELF-ASSEMBLED LIQUID DILUTABLE VEHICLES

FIELD OF THE INVENTION

This invention relates to nano-sized self-assembled structured concentrates and their use as carriers of active materials.

BACKGROUND OF THE INVENTION

Administering of active components into the human body requires the use of an appropriate vehicle for bringing an effective amount of the active component intact to the desired site in the human body. The desired site varies and it may be the blood stream, organs, cells etc. Active components that dissolve very poorly in oil or water pose a problem as to the route for their administration, transport and reaching their target. Furthermore, many chemicals that can serve as appropriate vehicles for such active compounds cannot be used in association with the human body, i.e. their use is unsafe or even hazardous. Constructing the appropriate vehicle and the desired efficient formulation, poses a challenge to developers of new medicaments.

Nutraceuticals, which are food supplements with health benefits, are commonly used as part of the daily diet. Nutraceuticals are vitamins, minerals, extracts of natural components (for example plants, flowers, roots or leaves), which are not medicaments, yet are believed to have a positive effect on the human body. They may have a long-term effect or an immediate effect and may be used for long treatment of chronic, yet not terminal diseases.

Nutraceuticals may be used for example in order to lower blood pressure, reduce cancer risk factors, regulate the digestive tract system, strengthen immune systems, regulate growth, regulate sugar concentration in blood, lower cholesterol levels, serve as antioxidant agents and more. Antioxidants can donate electrons to quench and neutralize free radical oxygen molecules, which play an important role in the initiation and promotion of atherosclerosis, cancer, cataract, arthritis and other degenerative diseases. Antioxidants can be (i) water-soluble such as vitamin C, simple phenois, polyphenois, bioflavonoids, rosmarinic acid, catechins, or (ii) oil-soluble (lipophilic) such as vitamin E, $C_0$–$Q_{10}$ (coenzyme $Q_{10}$, ubiquinone), vitamin D, vitamin $B_{12}$, carotenoids (lycopene, β-carotene, lutein), etc.

Examples of health benefits of some Nutraceuticals are: (i) Lycopene may protect against coronary vascular disease, reduce risk factors of prostate cancer, shrink tumors and reduce risk of upper digestive tract cancers. (ii) Lutein, in addition to its antioxidant activity, reduces the incidence of cataract limits blue light damage and reduces age-related macular degeneration and (iii) Phytosterols are used for reducing cholesterol adsorption.

Although the use of nutraceuticals in capsules and tablets is abundant, their effect is frequently diminished or even lost since many of the nutraceuticals are not soluble in water, vegetable oils or food-grade solvents. Due to their low solubility, they cannot penetrate into the mete therefore their bioavailability is very poor.

A common approach for constructing an appropriate vehicle for transporting nutraceuticals, medicaments, peptides or proteins is the use of microemulsions. In the microemulsion, the active compounds are not soluble but rather are solubilized. The general concept of solubilization of active components and its utilization may be found in the following review articles: 1. Solans, C., Pons, R., Kunieda, H "Overview of basic aspects of microemulsions" *Industrial Applications of Microemulsions*, Solans, C., Kunieda, H. Eds.; Dekker: New York, (1997); 66:1-17; 2 Dungan, S. R. "Microemulsions in foods: properties and applications" ibid 148–170; 3. Holmberg, K. "Quarter century progress and new horizons in microemulsions" in *Micelles, Microemulsions and Monolayers*, Shah, 0. Ed.; Dekker: New York (1998) 161–192; 4. Garti, N., "Microemulsions, emulsions, double emulsions and emulsions in food" in *Formulation Science* (proceeding from formulation forum '97-association of formulation chemists) (1998) 1, 147–219; 5. Ezrahi, S., Aserin, A., Garti, N. in *Microemulsions-fundamental wad applied aspects* Kumar, P. and Mittal, K. L. Eds. Marcel Dekker, Inc. New York (1999) "Aggregation behavior in one-phase (Winsor IV) systems" 185–246; 6. Garti, N., Clement, V., Leser, M., Aserin, A. Fanun, M. "Sucrose esters microemulsions J. Molec. Liquids (1999) 80, 253–296.

U.S. Pat. No. 6,063,762 describes a microemulsion for cyclosporin, consisting of oil, surfactant and a lipophilic solvent comprising of an ester of polycarboxylic acid and/or carboxylic acid ester of polyols. GB 588,298 describes a system for solubilizing lipoid soluble vitamins, comprising of polyalkylene oxide derivative of a partial fatty acid (more than $C_{12}$) and an ester of polyhydric alcohol, where the resulting solution is miscible in water or aqueous solutions. U.S. Pat. No. 5,725,803 discloses a new emulsifier for a water/oil system, comprising of phytosterol, 5–23 wt % $C_{20-24}$-alkyl alcohol and a mixture of $C_{10-28}$-fatty alcohols. WO 99/53,925 describes a composition comprising of phytosterols and lecithin which is dispersed in water by shaking, vortexing, sonicating or passing through a small orifice. WO 99/39,715 describes yet another system for solubilizing phytosterols by macromolecules, such as starch or saccharides.

Ultramicroemulsions and their use in pharmaceutical preparations are described in U.S. Pat. No. 6,057,359 as an aqueous ultramicroemulsion, in U.S. Pat. No. 5,536,504 for ultramicroemulsions containing xanthophyll esters, in U.S. Pat. No. 6,180,661 where flavanol-glycoside per-esters are used for achieving an ultramicroemulsion, and in U.S. Pat. No. 6,248,363.

SUMMARY OF THE INTENTION

The present invention is based on the findings of novel nano-sized self-assembled structured concentrates that can solubilize lipophilic compounds. The nano-sized self-assembled structured concentrates may be an aqueous continuous phase, an oil continuous phase or a bicontinuous phase. The novel nano-sized self-assembled structured concentrates may be diluted either in water or in oil to any desirable dilution while maintaining their structure. The nano-sized self-assembled structured concentrates may be used as effective suitable carriers for transferring active components into the human body.

Thus in one aspect the invention is directed towards nano-sized self-assembled structured liquid concentrates comprising of:
(i) water;
(ii) a polyol co-solvent selected from the group consisting of alcohols, polyalcohols, aldehydes, ketons, thiols, mono- and di-saccharides;
(iii) at least one surfactant yielding a surfactant of hydrophilic nature;
(iv) co-surfactant selected from $C_{2-16}$-alcohols; and
(v) oil phase being a solvent selected from the group consisting of long chain alcohols $C_{5-18}$, $C_{2-12}$-ketone, $C_{2-12}$- aldehyde, $C_{2-24}$-fatty acid or their esters, glycerol mono, di and tri-esters, terpene, terpin, terpinene, limonene, penta- or -tetracyclic triterpenic alcohols, sterol, alkylsterol, essential oil oleoresins, fat soluble lipidic vitamins, fennel oil, ginger oil, lavender oil, eucalyptus oil, anise oil, lemon oil, mandarin oil, peppermint oil, oregano oil, lime oil, tangerine oil, spearmint oil, triethyl citrate, ethyl oleate, ethyl caprylate, anisole, anisol alcohol, benzyl acetate, benzyl alcohol, benzyl propionate, ethyl lactate, phenethyl alcohol. Terpenes and camphors selected from α-pinene, borneol, camphour, cineole, carvone, terpineol, menthol, menthone, thymol, geraniol, citral, terpinolene, hemonene, citronellal. Other natural flavoring materials selected from linalool, eugenol, vanillin. Synthetic flavoring materials selected from hexyl alcohol, hexyl aldehyde, benzaldehyde, cinnamic aldehyde, citronellyl butyrate, nerol, phelandrene, phenyl ethyl acetate, ethyl propionate, ethyl laurate, ethyl decanoate, ethyl butyrate, ethyl hexanoate, ethyl caprylate, brandy flavoring oil, apple flavoring oil, paprica flavoring oil, blackberry flavoring oil, blueberry flavoring oil, honey flavoring oil, licorice flavoring oil, maple flavoring oil, strawberry flavoring oil, watermelon flavoring oil; wherein said solvent may further comprise at least one co-solvent selected from fatty acids, fatty alcohols, sterols, terpins, terpenines, essential oils, vitamins.

In a yet further aspect the present invention is directed to a nanosized structured liquid concentrate for use as a suitable carrier for oil-soluble, oil non-soluble or water-soluble nutraceuticals, food supplements, food additives, plant extracts, medicaments, peptides, proteins or carbohydrates. Thus the present invention is directed to nanosized structured liquid concentrates comprising therein oil soluble, oil non-soluble or water-soluble material selected from the group consisting of nutraceuticals, food supplements, food additives, plant extracts, medicaments, peptides, proteins or carbohydrates. In a preferred embodiment the nutraceuticals are selected from lutein, lutein esters, β-carotene, lycopene, Co-$Q_{10}$, flax seed oil, lipoic acid, phytosterols, α- and γ-polyunsaturated fatty acids, vitamin D, vitamin $B_{12}$.

In a yet further aspect the present invention is directed to food products, medicaments or cosmetic preparations comprising the nano-sized self-assembled * structured concentrates as an aqueous phase, as an oil phase or as a bicontinuous phase dilutable to any desirable extent.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 4A shows the ternary phase diagram indicating the ratio of the oil phase to the surfactant. FIG. 4B shows the effect of aqueous-based dilution and solubilization of lycopene. FIG. 4C shows the efficiency of the solubilization by the t-factor. FIG. 4D shows various a-factors as a function of Various surfactants.

FIG. 5A shows the ternary phase diagram indicating the ratio of the oil phase to the surfactant. FIG. 5B shows the effect of dilution and solubilization of phytosterol. FIG. 5C shows the efficiency of the solubilization by the α-factor. FIG. 5D shows various α-factors as a function of various surfactants.

FIG. 6A shows the ternary phase diagram indicating the two possibilities of the ratio of the oil phase to the surfactant. FIG. 6B shows the maximum solubilization reached in these two microemulsion systems. FIG. 6C shows the solubility normalized to the surfactant in the two possible nano-sized structure systems. FIG. 6D shows the solubility normalized to the oil in the two nano-sized structure systems.

DETAILED DESCRIPTION OF THE INVENTION

Figure 1A:
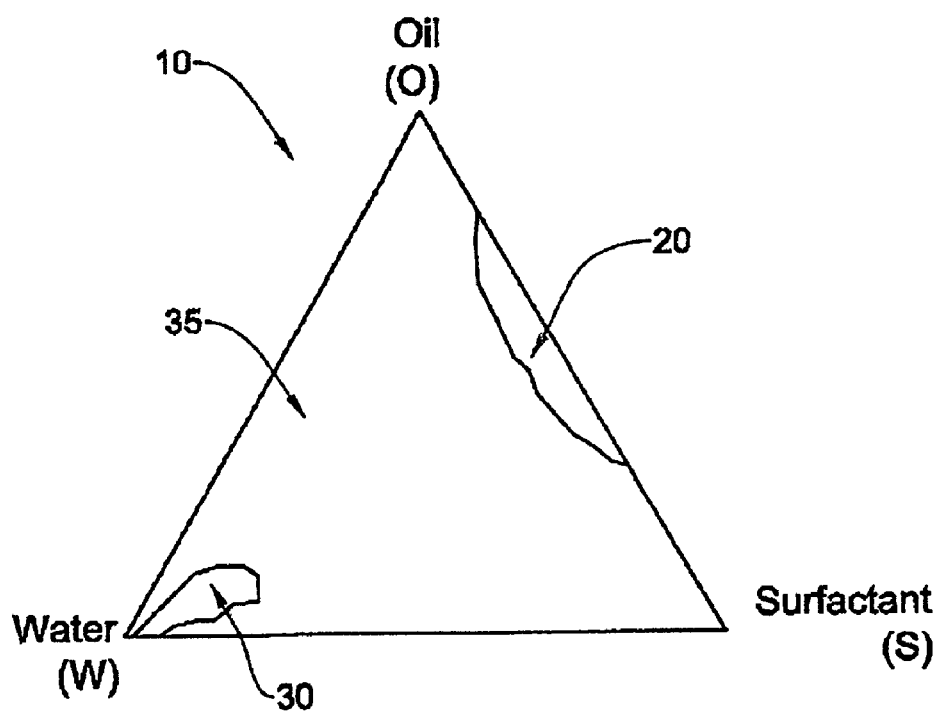
FIGS. 1A and 1B shows two phase diagrams of the prior art. 1A shows a phase diagram having two small isotropic areas, one where the water is the continuous phase and one where the oil is the continuous phase, separated by a large two-phase region. 1B shows a phase diagram where the oil/water consists essentially of two-phase and a single phase prevails only at the case where there is practically no oil.
Figure 1B:
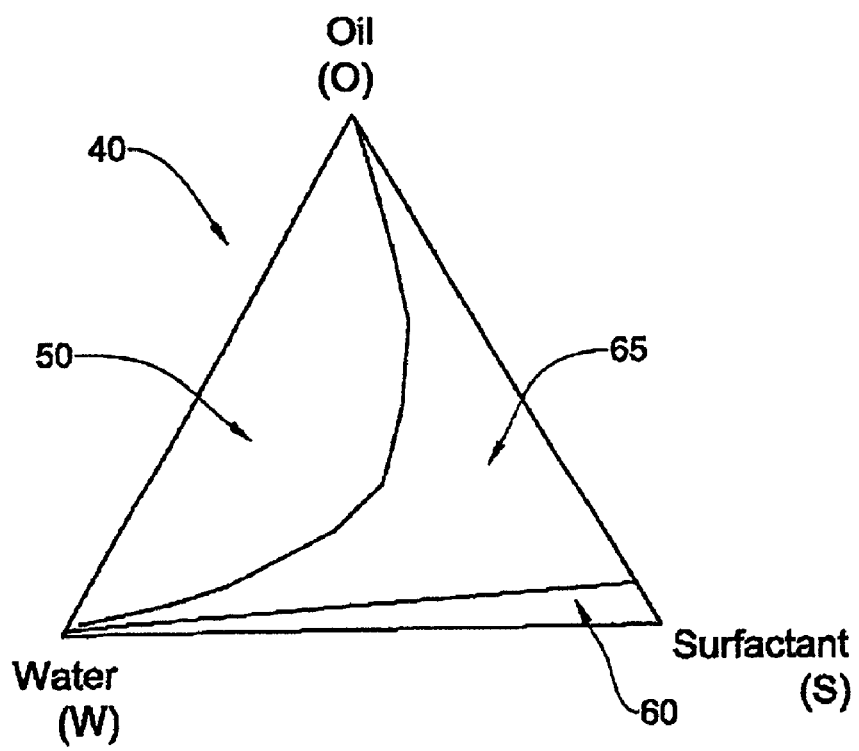
Figure 2:
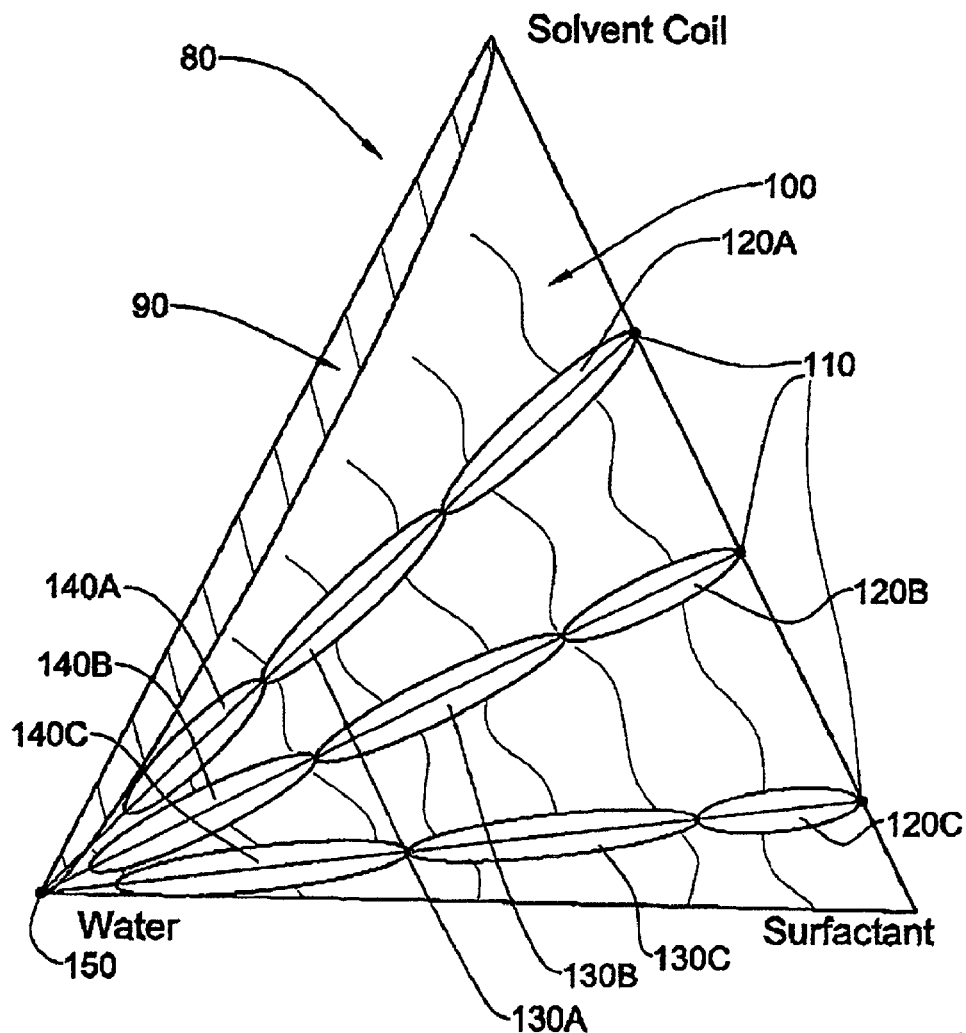
FIG. 2 shows a general ternary phase diagram for a system composed according to the present invention. The 2-phase region is small and the single phase region is a continuous phase of both oil and water demonstrating the possibility of diluting.
Figure 3:
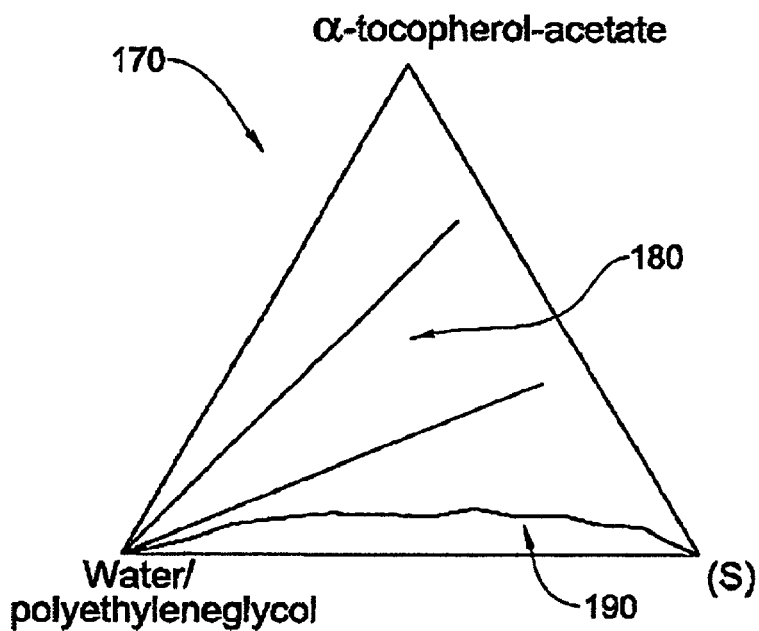
FIG. 3 shows a ternary phase diagram for a system comprising a particular solvent according to the invention.
Figure 4A:
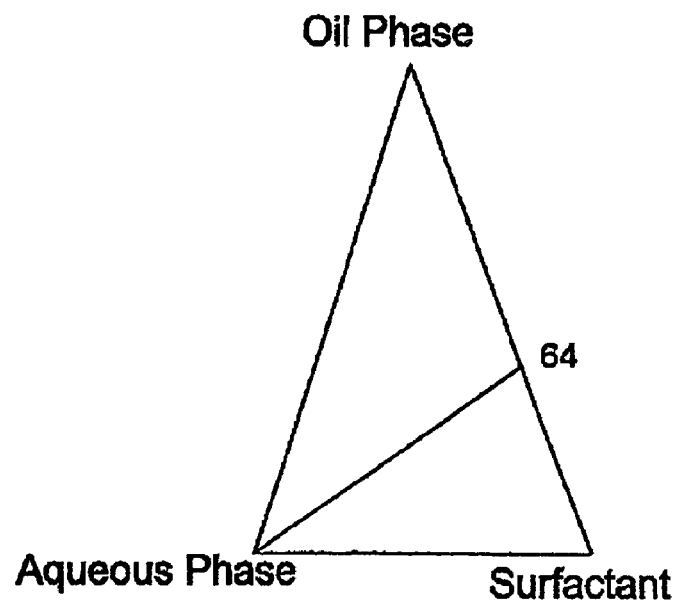
FIGS. 4A, 4B, 4C and 4D show the effect of dilution of lycopene in a system of the present invention.
Figure 4B:
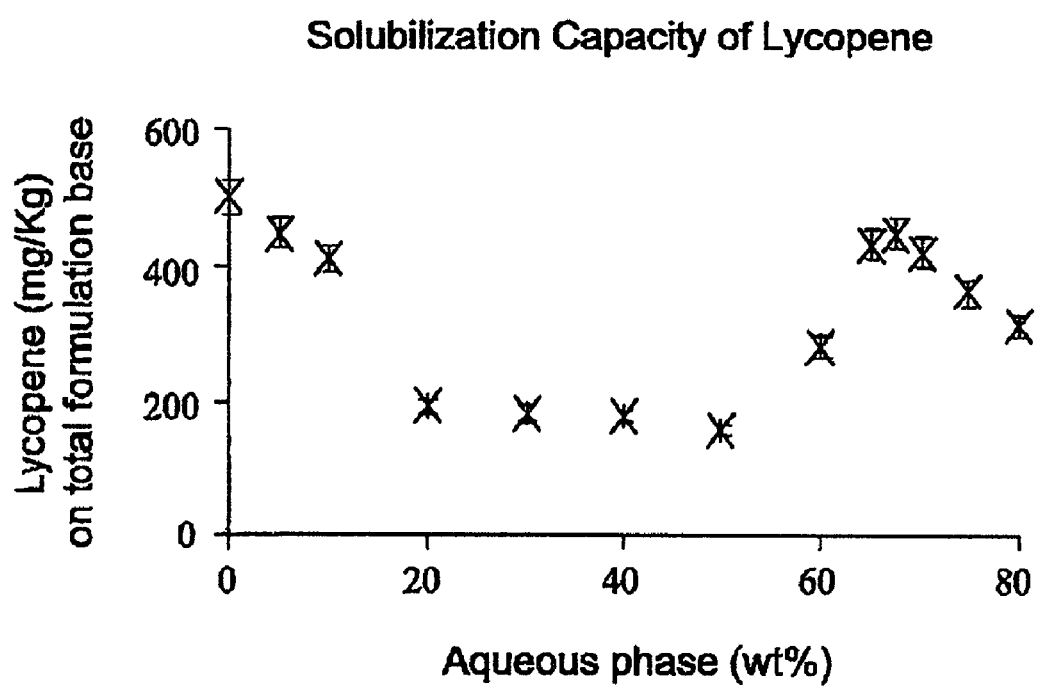
Figure 4C:
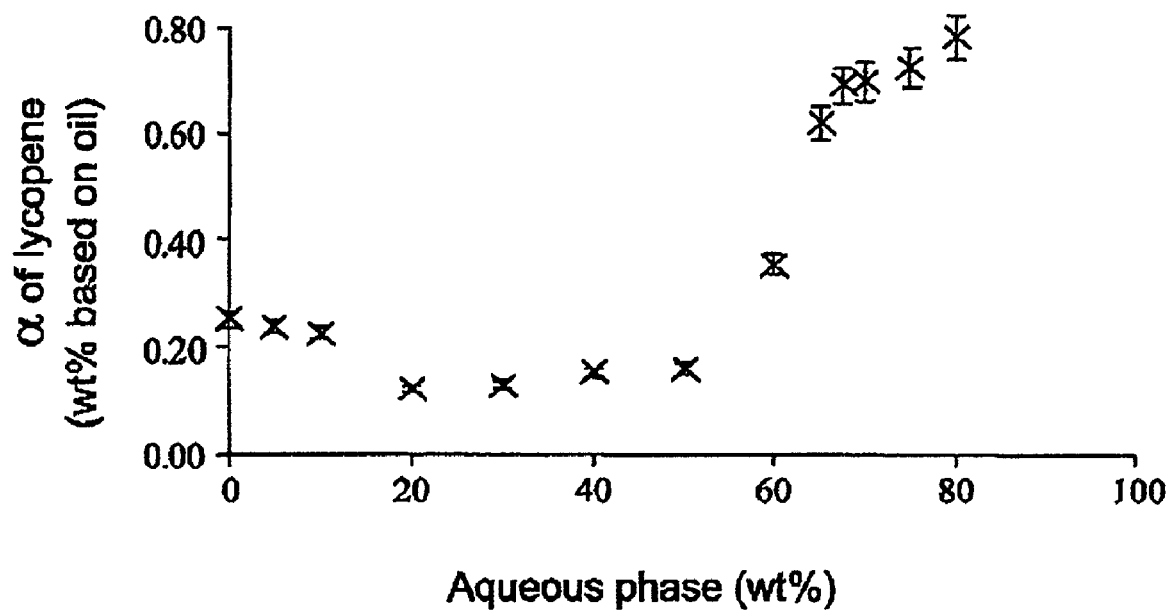
Figure 4D:
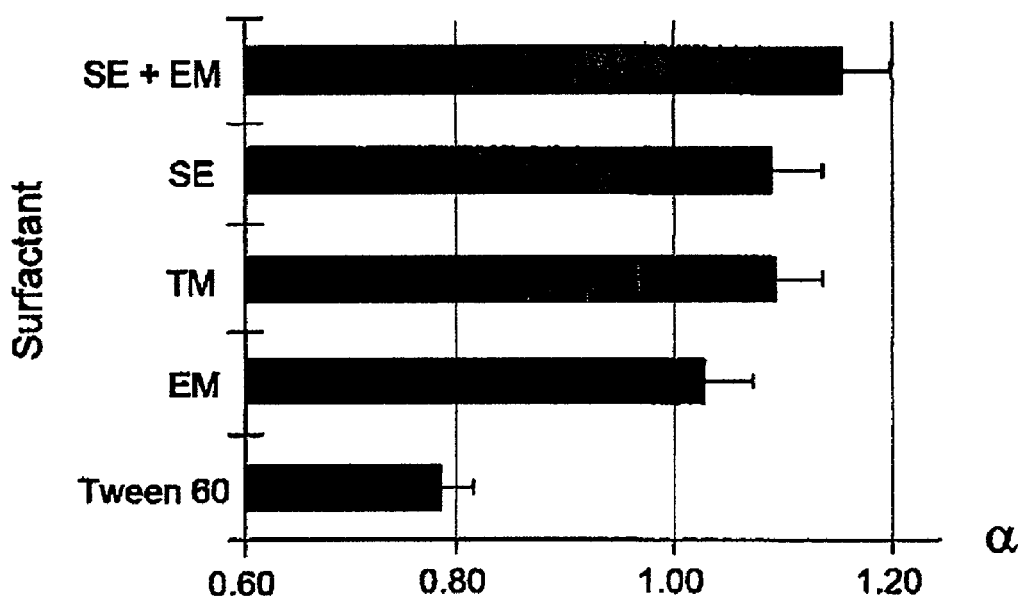

The invention will now be described with reference to some non-limiting specific embodiments. The invention will first be illustrated in reference to the attached drawings to be followed by a more detailed description below. Turning to FIG. 1, there are shown two different phase diagrams (1A and 1B) of ternary systems comprising oil/water/surfactant according to the prior art. Such a ternary system forms microemulsions. As a function of the relative amounts of each of the three components one may achieve a two-phase or a mono-phase liquid concentrate comprising of the microemulsion where the boundaries of the stable phases depend on the relative concentration of each component. In FIG. 1A there is illustrated a ternary phase diagram 10 exhibiting a rather small isotropic stable water in oil (W/O) composition phase at 20 and an even smaller stable oil in water (O/W) phase at 30. A two-phase region at equilibrium, at 35, prevails at all other concentrations of the ternary system. FIG. 1B illustrates yet another ternary phase diagram 40 exhibiting a rather large two-phase concentrate (non-stable) 50 and small two-phase region at 60. A one phase stable isotropic region exists at 65. Turning to FIG. 2, a general ternary phase diagram 80 describing the nano-sized self-assembled structured concentrates of the present invention, A rather small two-phase concentrate region 90 and a large stable one-phase at 100 region are present. A micellar concentrate of the nano-sized self-assembled structures exists at 110, i.e. there is no aqueous phase. Adding a small amount of aqueous phase results in an oil continuous phase, which is actually water in oil (W/O) region at 120A, 120B and 120C along the tree dilution lines. Addition of an increasing amount of aqueous solution results in a bi-continuous region at 130A, 130B and 130C along the three dilution lines. At the point where the amount of aqueous solution is greater than that of the oil phase there exists an aqueous continuous phase, which is actually an oil in water (O/W) region generally at 140A, 140B and 140C along the three dilution lines. Direct micelles exist only at the extreme at 150. It should be noted that along each concentration line as the concentration of the surfactant increases, the oil continuous phase may decrease is size while the bicontinuous and water continuous phases may increase in size. Turning to FIG. 3, a ternary phase diagram 170 describing another nanosized-structured concentrate of the present invention is shown. The oil phase, which is the desired solvent for achieving a single-phase system, is α-tocopherol acetate. The aqueous system comprises of water and a co-solvent—propylene glycol. As shown, a major portion of the four-component system is in one stable region 180, while only a minor portion 190 is a two-phase system. Phase diagrams, solubilization factors and efficiency of solubilization for lycopene, phytosterol and lutein in ternary systems according to lo the present invention are given in FIGS. 4–6. In particular, FIG. 4A shows a phase diagram of a system for solubilizing lycopene, wherein the system is comprised of an aqueous phase comprising water/propylene glycol in a 1:1 ratio, an oil phase comprising of limonene/ethanol in a 1:1 ratio, and Tween 60 as the surfactant, where the ratio of the surfactant to the oil phase is 3:2 (indicated as the 64 line). It should be noted that the ratio between each of the components of the oil phase to the surfactant is 1:3. FIG. 4B shows the solubility capacity of lycopene (milligrams) in 1 Kg of nano-sized self-assembled structured concentrate, where the maximum solubility is 450 mg, i.e. maximum solubilization is 0.45% (wt) reached at the point where the aqueous phase is about 67% of the composition. As shown, upon further dilution with water, tie solubilization of lycopene drops over the dilution factor. In case the system is diluted from 67% water to 80% water, the dilution factor (from inversion) is 80/67=1.19. The solubilization on the other hand decreases by a factor of 450/312.5=1.44. This indicates structural change in the nano-sized self-assembled concentrates. Turning to FIG. 4C, the efficiency of the solubilization in the described system is represented (α). The efficiency factor, α, is defined as lycopene/oil(wt/wt)X 100. As shown, the maximum solubilization on an oil base is 0.8 wt %. Thus the nano-sized structured system of the present invention succeeds in solubilizing lycopene up to 17.7 fold of the oil dissolution capacity e.g. 0.8/0.045 (the solubility of lycopene in oil is ca. 0.045 wt %). Tuming to FIG. 4D, there is shown the solubilization capacity of the lycopene as a function of the nature of the surfactant system. As shown, for the case where the surfactant is Tween 60, the efficiency factor (solubilization based on the oil phase) is 0.8 wt %. However, this value is increased to 1.05, 1.1, 1.1 and 1.16 (wt %) for the cases where the surfactant is ethoxylated monoglycerides (EM), triglycerol monooleate (TM), sugar ester (SE), and a mixture of SE+EM, respectively. It should be noted that such efficiency factors are equivalent to a solubilization factor of up to 25 fold.

Figure 5A:
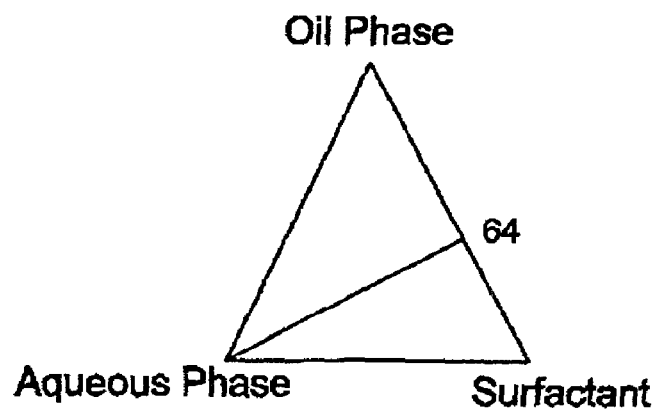
FIGS. 5A, 5B, 5C and 5D show the effect of dilution of phytosterol in a system of the present invention.
Figure 5B:
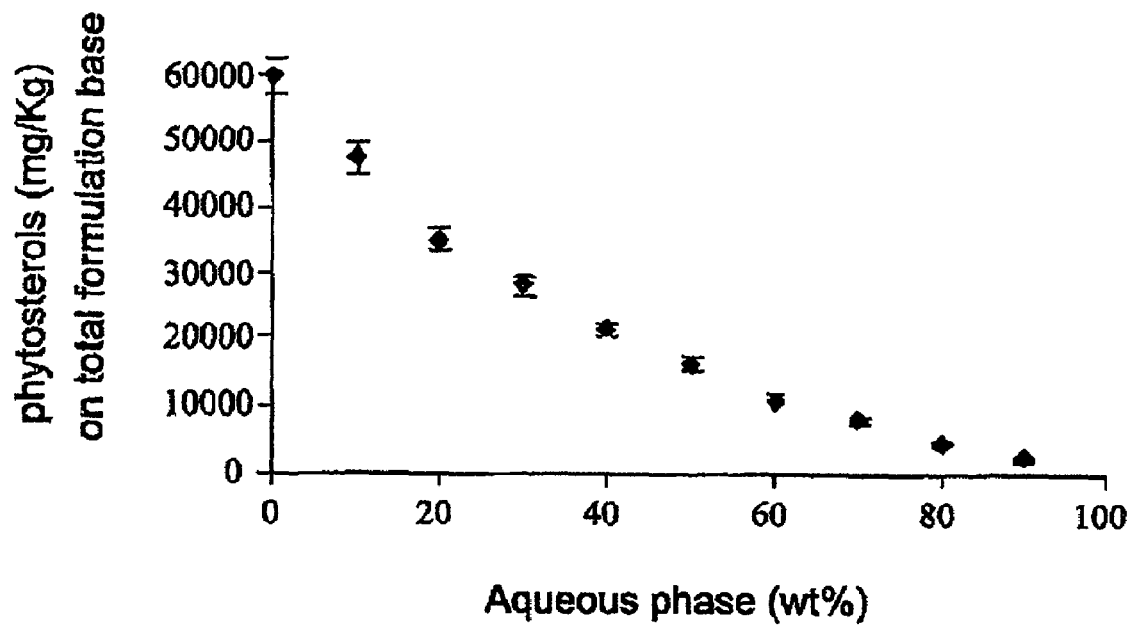
Figure 5C:
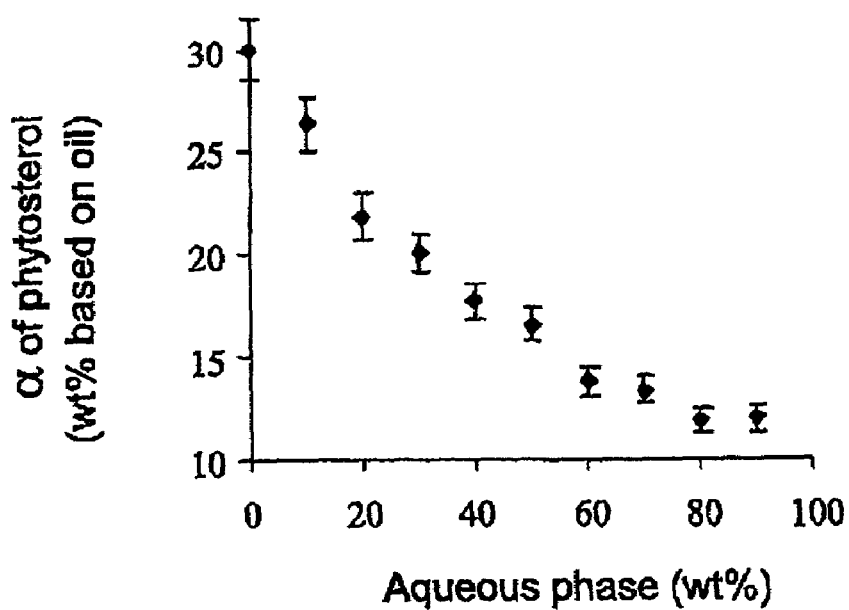
Figure 5D:
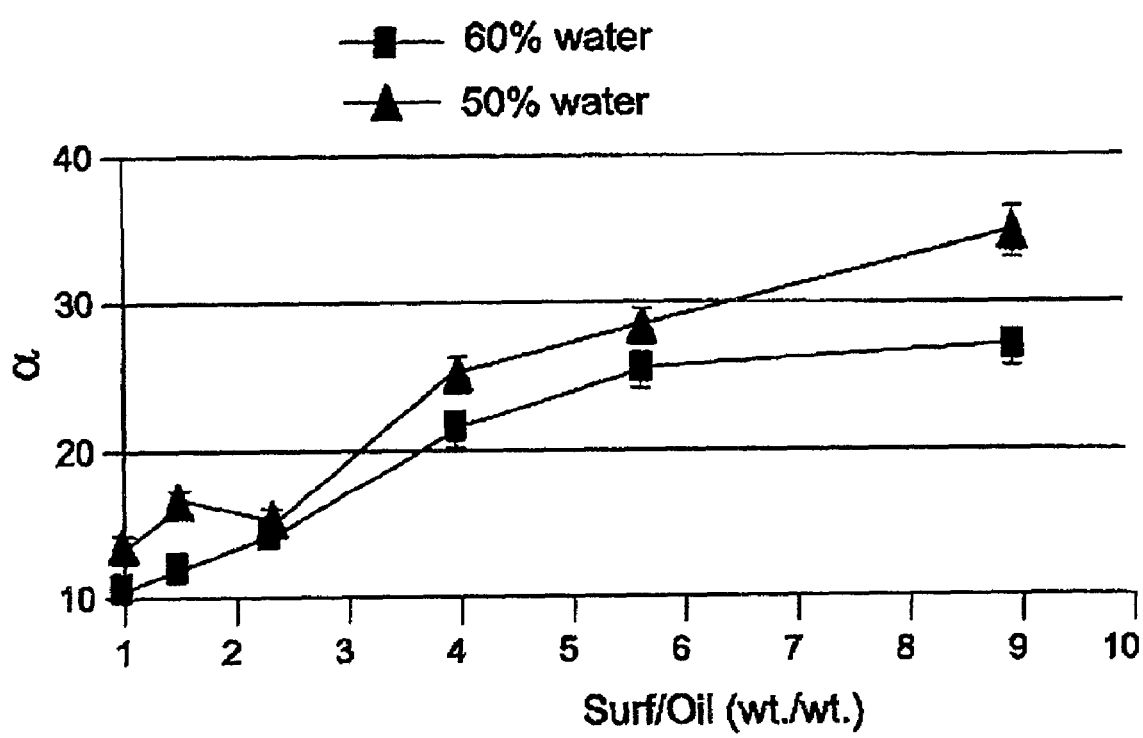
Figure 6A:
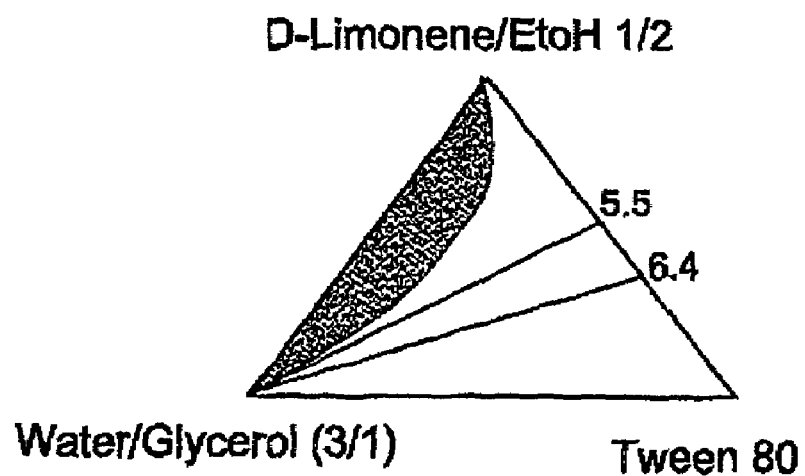
FIGS. 6A, 6B, 6C and 6D show the effect of solubilization of lutein esters in two nano-sized structures of the present invention.
Figure 6B:
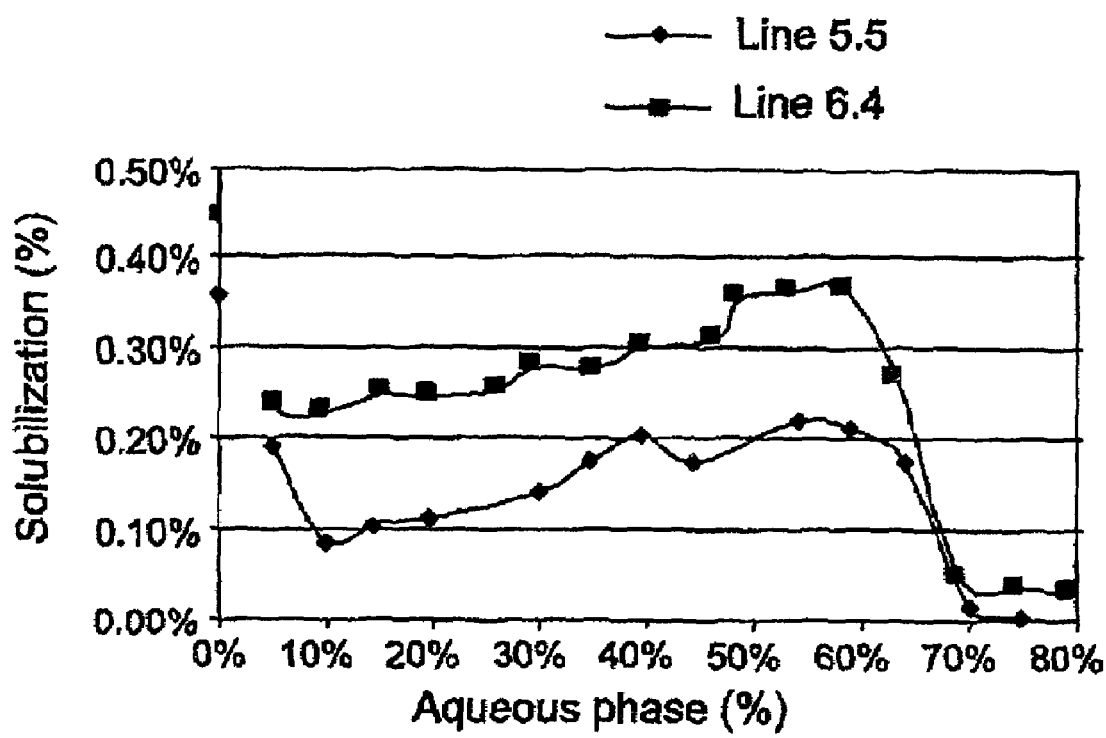
Figure 6C:
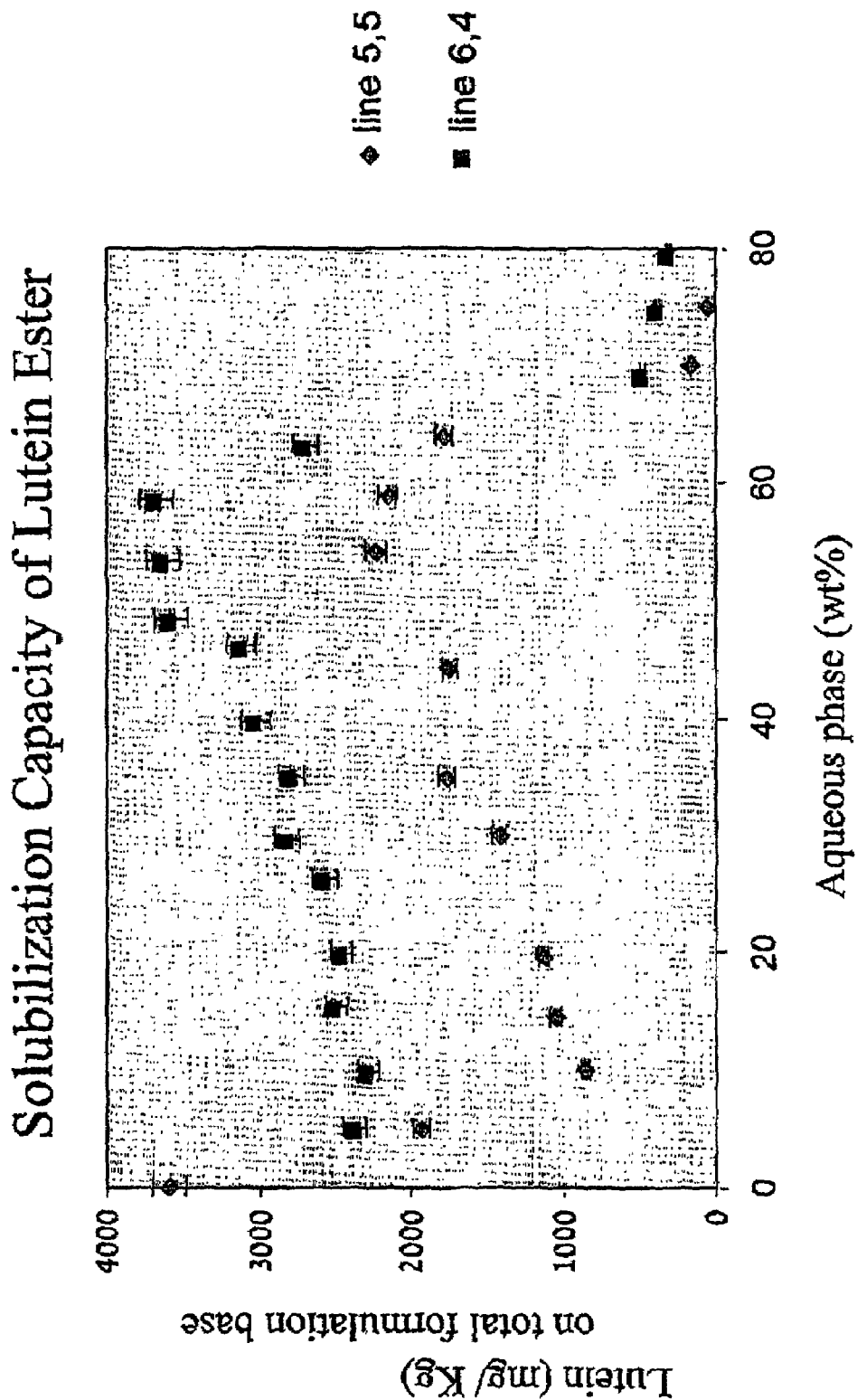
Figure 6D:
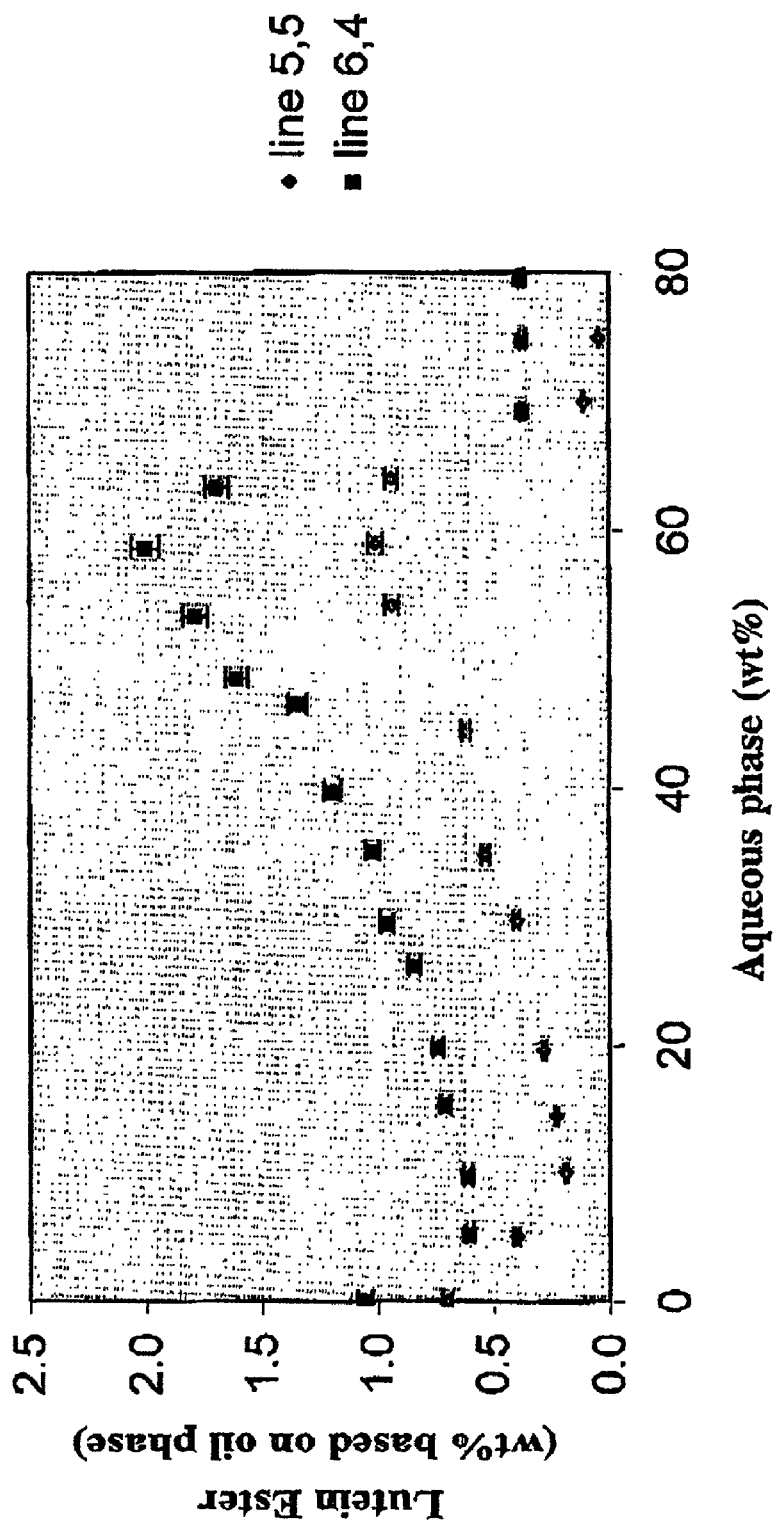
Figure 7A:
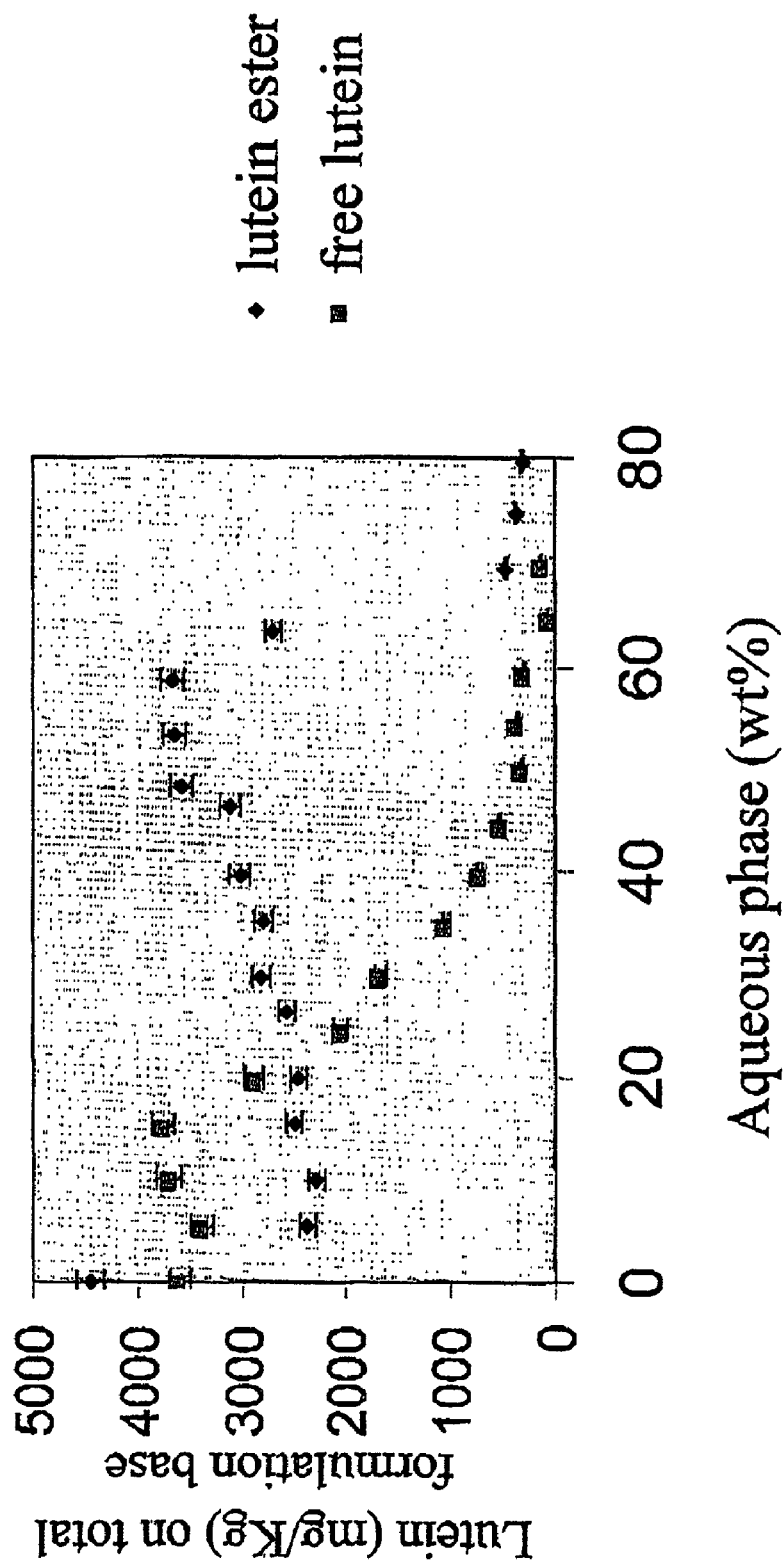
FIGS. 7A and 7D show the effect of solubilization of lutein ester compared to that of free lutein.
Figure 7B:
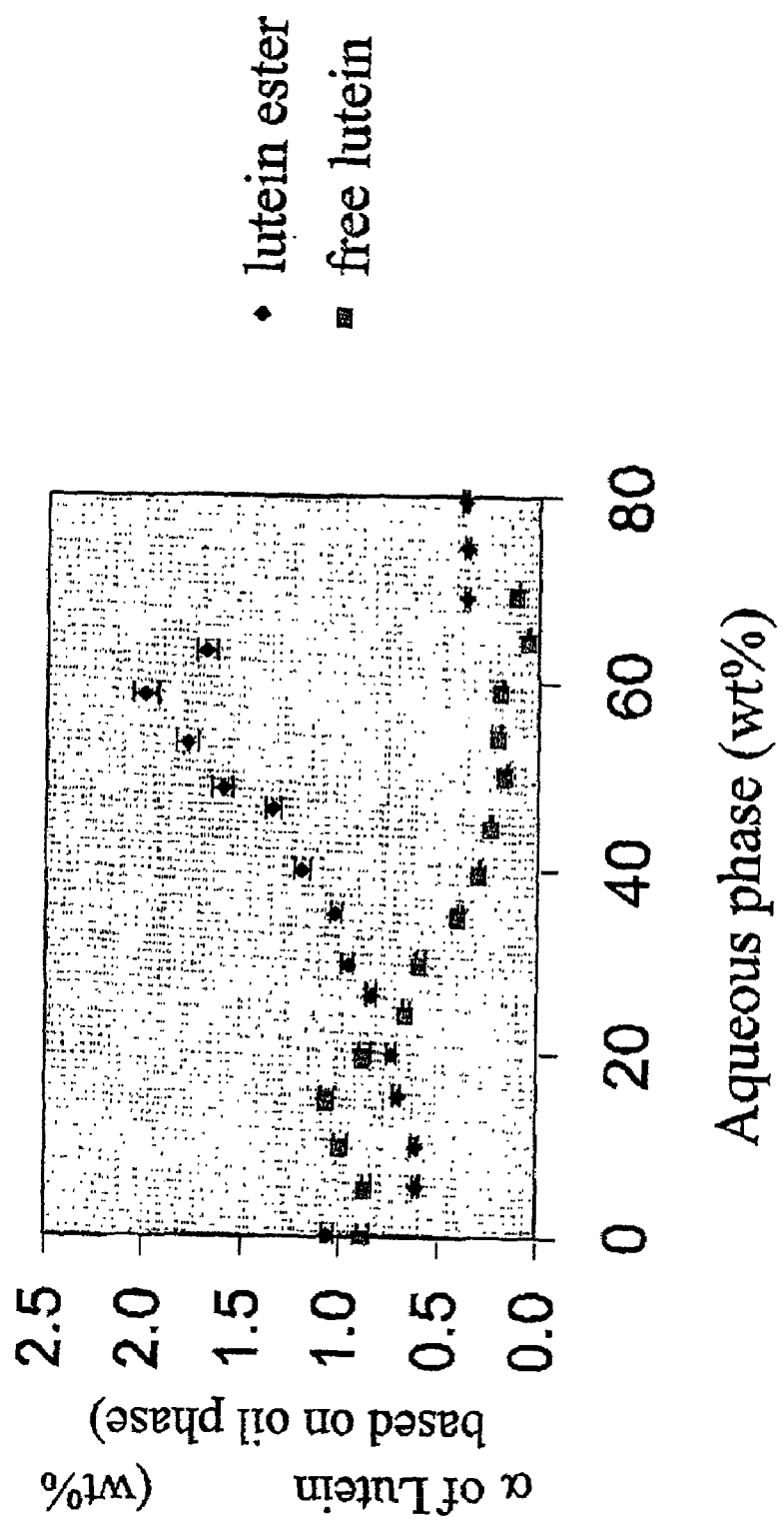

FIG. 5A shows a phase diagram of a system for solubilizing phytosterol. The system is comprised of an aqueous phase comprising water/propylene glycol in a 1:1 ratio, an oil phase comprising of limonene/ethanol in a 1:1 ratio, and Tween 60 as the surfactant, where the ratio of the surfactant to the oil phase is 3:2 (indicated as the 64 line). It should be noted that the ratio between each of the components of the oil phase to the surface is 1:3. The solubility capacity of such a system is given in FIG. 5B for a system comprising 1 Kg of nano-sized self-assembled structured concentrate. As shown, the maximum solubilization is 165 mg, i.e. maximum solubilization is 1.65% (wt) reached at the point where the aqueous phase is 50%. Upon dilution, the solubilization drops as demonstrated by the dilution of the system from 50% water to 80% water. The factor for the dilution is 80/50=1.3, while, as can be seen from the figure, the solubilization decrease factor is 165 mg/45 mg=3.6 or 0.165/0.045=3.6, once again demonstrating that upon dilution, the solubilization factor drops over the dilution factor. Turing to FIG. 5C, the efficiency of the solubilization in the described system is represented (α). The efficiency factor, α, is defined as phytosterol/oil(wt/wt)X 100. As shown the maximum solubilization on an oil base is 16.7 wt %. It should be noted that the solubilization decreases as the percentage of the aqueous phase increases. FIG. 5D illustrates the solubilization efficiency of phytosterol at different surfactant/oil ratio at two aqueous phase concentrations, 50% and 60%. The efficiency of solubilization of phytosteol increases for both aqueous concentrations as the ratio of the surfactant to oil increases. From FIGS. 5C and 5D it is apparent that the solubilization factors are 6, 7 for concentrate. Turning to FIG. 6A there is shown a phase diagram of a system for solubilizing lutein. The system is comprised of an aqueous phase comprising water/glycerol in a 3:1 ratio, an oil phase comprising of limonene/ethanol in a 1:2 ratio, and Tween 80 as the surfactant. The ratio of the surfactant to the oil phase may either be 1:1 or 3:2 (indicated as lines 5.5 or 6.4). It should be noted that such a system might display at different ratios of the components, a two-phase system (demonstrated by the shady area). FIG. 6B shows the maximum solubilization that can be achieved with increasing concentration of the aqueous phase in the two systems where the ratio of the oil phase to surfactant may be either 3:2 or 1:1. It is apparent from the findings that the maximum solubilization for the two systems occurs in the bi continuous region (ca. 40 to 60% aqueous solution). For both systems, in the region where oil in water system (O/W) prevails, i.e. where the concentration of the aqueous solution is over 50%, there is limited solubilization. FIGS. 6C and 6D show the solubilization efficiency of lutein normalized to the surfactant or oil concentration respectively, for both 5.5 and 6.4 systems. As shown, solubilization is enhanced as the concentration of the surfactant is increased. FIGS. 7A and 7B show a comparison of solubilization efficiency of lutein ester compared to that of free lutein normalized to the surfactant or oil concentration, respectively, for 6:4 system. Tie different solubilization profiles of the two compounds demonstrates that their solubilization should be done in different environments. While the free lutein should be solubilized in a water in oil environment, the ester should be solubilized in a oil in water environment. As demonstrated in FIG. 2 the nano-sized self-assembled concentrates of the present invention may either be an aqueous phase or an oil phase, thus these two compounds may be solubilized efficiently.

The present invention provides novel nano-sized self-assembled structured concentrates formed by mixing of an oil phase, an aqueous phase and a surfactant. The ternary system forms nano-sized concentrates that are different than the classical microemulsion concentrate in their size and shape, being in the range of 1.5–80 nM which is 2–3 orders of magnitude lower than tat of classical emulsions, microemulsions or self-assembled structured concentrates. The nano-sized concentrates of the present invention enable in an efficient manner the solubilization, transport and dilution of oil-soluble, oil non-soluble or water-soluble nutraceuticals, food supplements, food additives, plant extracts, medicaments, peptides, proteins or carbohydrates. Thus they may be used as efficient vehicles for transport of active materials into the human body. The capability of these nano-sized self-assembled structured concentrates to solubilize the desired active component exceeds many-fold the solubility capacities of the aqueous or oil phase alone or of the aqueous or oil phase in the presence of an appropriate surfactant. As shown in FIGS. 4–6 for lycopene, phytoserol and lutein, respectively, the increase is in the range of 7–20 fold. Furthermore, the nano-sized self-assembled structured concentrates, once formed, may be diluted as desired in either oil or water while a single phase is maintained and the nano-sized structured concentrate is intact. The aqueous phase comprises of water, co-surfactants and a polyol co-solvent. The co-surfactant is selected from $C_{2-16}$-alcohols, most preferred are ethanol, propanol, butanol or pentanol or their mixtures. Non-limiting examples of the polyol co-solvent are aldo- or keto- sugars, oligomeric carbohydrates such as glycerol, ethylene glycol, propylene glycol, sorbitol, xylitol, glucose, and fructose. The oil phase is comprised of a solvent and may ether comprise a co-solvent. The solvent is selected from the group consisting of $C_2$–$C_6$-alcohol, long chain fatty alcohols, $C_2$–$C_6$-ketone, $C_2$–$C_6$-aldehyde, $C_{2-24}$-fatty acid or their esters, terpene, terpin, terpinene, limonene, penta- or -tetracyclic triterpenic alcohols, sterol, alkylsterol, essential oil, fat soluble lipidic vitamins, fennel oil, ginger oil, lavender oil, eucalyptus oil, anise oil, lemon oil, mandarin oil, peppermint oil, oregano oil, lime oil, tangerine oil, spearmint oil, triethyl citrate, ethyl oleate, ethyl caprylate, anisole, anisol alcohol, benzyl acetate, benzyl alcohol, benzyl propionate, ethyl lactate, phenethyl alcohol. Terpenes and camphors like α-pinene, borneol, camphour, cineole, carvone, terpineol, menthol, menthone, thymol, geraniol, citral, terpinolene, hemonene, citronellal. Other natural flavoring materials like linalool, eugenol, vanillin. Synthetic flavoring materials like hexyl alcohol, hexyl aldehyde, benzaldehyde, cinnamic aldehyde, citronellyl butyrate, nerol, phelandrene, phenyl ethyl acetate, ethyl propionate, ethyl laurate, ethyl decanoate, ethyl butyrate, ethyl hexanoate, ethyl caprylate, brandy flavoring oil, apple flavoring oil, paprica flavoring oil, blackberry flavoring oil, blueberry flavoring oil, honey flavoring, oil, licorice flavoring oil, maple flavoring oil, strawberry flavoring oil, watermelon flavoring oil. Preferably, the solvent is selected from D-limonene, tocopherol, tocopherol-acetate or triacetin. The co-solvent is selected from the group consisting of fatty acids, fatty alcohols, sterols, terpins, terpenines, essential oils, vitamins, where the co-surfactant may serve as a co-solvent. The at least one surfactant is hydrophilic in nature and non limiting examples are ethoxylated castor oil, ethoxylated sorbitan esters such as ethoxylated sorbitan -monostearate, -monooleate or monolaurate. They may also be sucrose ester, poly glycerol esters such as mono, did, tri, tetra and up to decal (named poly) glycerol (termed polyglycerol) esters of lauric ($C_{12}$); myristic ($C_{14}$); palmitic ($C_{16}$); stearic ($C_{18}$); oleic ($C_{18:1}$); linoleic ($C_{18:2}$); and their combinations or of any fatty acids polyglycerol, poly fatty acids) and ethoxylated mono-diglycerides. The hydrophilic nature of the added surfactant should be maintained although its extent may vary by combining two surfactants of different hydrophilic nature or even a hydrophilic surfactant with a hydrophobic surfactant to "dilute" the hydrophilic nature of the former surfactant. In case a hydrophobic surfactant is added it can be of any food grade surfactant, where non-limiting examples are sorbitan esters, sorbitan tristreate, monoglycerides, sucrose esters, ethoxylated castor oils, polyglycerol esters.

Upon the mixture of the above-mentioned components the desired nano-sized structured concentrates form spontaneously with structures having dimensions of 1.5–80 nM, typically 5–20 nM. Such nano-sized structured concentrates solubilize in efficient manner lipophilic compounds, as well as hydrophilic compounds. The nanosized-structured concentrates together with the desired active component comprised therein may be (as shown in FIG. 2) in the form of an aqueous continuous phase, an oil continuous phase or a bicontinuous phase. The aqueous continuous phase is comprised of (wt/wt) 0.1 to 40% oil phase, 0.01–40% active matter to be solubilized and 40–99.8% water-soluble matter. An oil continuous phase is comprised of (wt/wt) 0.01–40% water-soluble phase, 0.01–40% active matter to be solubilized. and 40–99.8% oil soluble mater. The bi-continuous phase is comprsed of (wt/wt) 20–60% oil soluble phase, 0.01–60% active matter to be solubilized and 20–60% water-soluble matter. Lipophilic compounds are non-soluble in aqueous systems and frequently also in food grade organic solvents such as vegetable oils or alcohols. Many of the known nutraceuticals, are lipophilic. Therefore, such compounds are difficult to dissolve or solubilize and therefore their bioavailability and bioefficacy are low. Such lipophilic compounds may be entrapped in appropriate vehicles, which enhance their transport from the guts to the blood stream and further through biological membranes. Micelles (direct and reverse), liposomes, microemulsions and bicontinuous phases are all known. Such vehicles are frequently limited in their use for a particular type of lipophilic compounds. The nano-sized structured concentrates of the present invention overcome such drawback by their versatility and capability to entrap lipophilic moieties and transporting the entrapped material through biological membranes, thus enhancing their bioavailability. The nano-sized structured concentrates of the present invention are isotropic transparent structured fluids, spontaneously formed, thermodynamically stable, of at least two immiscible liquids (water and oil) with the aid of a surfactant, co-surfactant and co-solvent. Their advantage is the large interfacial area that facilitates the solubilization of the lipophilic compounds and the fact they may be fully diluted in water or oil to any desirable dilution maintaining their structure despite the transition from water in oil (W/O) to oil in water (O/W) microenvironment. The nano-sized liquid concentrates form a clear and transparent liquid that shows no precipitates, crystalline matter or turbidity. The structured concentrate is of low viscosity, thermodynamically stable, does not separate, coalesce, aggregate, flocculate or cream at any ambient temperature even after prolonged storage. Additional properties of the novel nano-sized structured liquid concentrates are protection of the active matter entrapped therein against oxidation, hydrolysis, enzymatic (lipase) and bacterial attack. The vehicles further mask the taste, color and odor of the active material entrapped therein. In a preferred embodiment all components are of food-grade, as the nanosized concentrates of the present invention in a preferred mode are used as vehicles for active components to be administered into the human body. The desired active component is trapped within the nanosized structure boundary, where the transition from micellar to O/W to W/O results only in the migration of the active compounds within the nanostructured vehicle. The resulting nano-sized self-assembled concentrates after their formation may be diluted as desired in either oil or water. Such versatility of dilutions while maintaining stable single phases, i.e. retaining a stable solution which does not separate to its constituents has profound implications. The nutraceutical, food supplement, food additive, plant extract medicament, peptide, protein or carbohydrate may be entrapped in the nano-sized structured concentrate and incorporated into any known food product, medicament, cosmetic preparation solution maintaining its stability.

The invention will now be described by the following non-limiting examples.

EXAMPLES

Maximum solubilization of the nutraceuticals, lycopene, phytosterol, CO-$Q_{10}$ and lutein is given. Solubilization may be done according to the present invention in concentrate (micelle like structure), in water-rich phase, as a bicontinuous phase and in oil-rich phase. The following Tables exemplify the concentrations of the nutraceuticals in each system.

A. Lycopene Solubilization

| A.1: Micellar concentrate: | |
| --- | --- |
| Component | Concentration (%) |
| [1]lycopene | 0.05 (and up to 10% oleoresin of tomato or any other oleoresin) |
| R(+)-limonene | 19.8 |
| ethanol | 19.8 |
| Tween 60 | 59.5 |
| PG | 0 |
| Water | 0 |

[1]Oleoresin containing 6% of lycopene.

| A.2: 30% aqueous phase (O/G nano-sized structures) | |
| --- | --- |
| Component | Concentration (%) |
| [1]lycopene (in oleoresin) | 0.018 |
| R(+)-limonene | 13.96 |
| ethanol | 13.96 |
| Tween 60 | 41.87 |
| PG | 14.95 |
| water | 14.95 |

[1]Oleoresin containing 6% of lycopene.

| A.3: 70% aqueous phase (O/W nano-sized structures) | |
| --- | --- |
| Component | Concentration (%) |
| [1]lycopene | 0.042 |
| R(+)-limonene | 5.96 |
| ethanol | 5.96 |
| Tween 60 | 17.89 |
| PG | 34.79 |
| water | 34.79 |

[1]Oleoresin containing 7% of lycopene.

B. Phytosterol Solubilization

It should be noted that solubilization of phytosterol may be done at any level of water (0 to 99%), however the amount of the solubilizate corresponds to its maximum solubilization according to FIG. 5. Furthermore, pure free phytosterol (98%) does not require solubilization in other solvents.

| B.1: Micellar concentrate | |
| --- | --- |
| Component | Concentration (%) |
| phytosterol | 5.67 |
| R(+)-limonene | 18.6 |
| ethanol | 18.6 |
| Tween 60 | 56.61 |
| PG | 0 |
| water | 0 |

| B.2: 30% aqueous phase (W/O nano-sized structures) | |
| --- | --- |
| Component | Concentration (%) |
| phytosterol | 2.91 |
| R(+)-limonene | 13.6 |
| ethanol | 13.6 |
| Tween 60 | 40.77 |
| PG | 14.56 |
| water | 14.56 |

| B.3: 70% aqueous phase (O/W nano-sized structures) | |
| --- | --- |
| Component | Concentration (%) |
| phytosterol | 0.8 |
| R(+)-limonene | 5.95 |
| ethanol | 5.95 |
| Tween 60 | 17.86 |
| PG | 34.72 |
| water | 34.72 |

C: Co-$Q_{10}$ Solubilization

| C:1 Micellar concentrate | |
| --- | --- |
| Component | Concentration (%) |
| Co-$Q_{10}$ | 2.45 |
| R(+)-limonene | 17.22 |
| ethanol | 31.67 |
| Tween 80 | 48.66 |
| water | 0 |
| glycerol | 0 |

| C.2: 30% aqueous phase (W/O nano-sized structures) | |
| --- | --- |
| Component | Concentration (%) |
| Co-$Q_{10}$ | 1.04 |
| R(+)-limonene | 12.08 |
| ethanol | 22.05 |
| Tween 80 | 35.14 |
| water | 22.51 |
| glycerol | 7.18 |

| C.3: 70% aqueous phase (O/W nano-sized structures) | |
|---|---|
| Component | Concentration (%) |
| Co-$Q_{10}$ | 0.45 |
| R(+)-limonene | 5.25 |
| ethanol | 9.98 |
| Tween 80 | 15.28 |
| water | 51.78 |
| glycerol | 17.26 |

D. Lutein Solubilization

| D.1: Micellar concentration (0% aqueous phase) | | | |
|---|---|---|---|
| Component | Concentration(%) | Component | Concentration(%) |
| D-limonene | 13.5 | R(+)-limonene | 13.16 |
| ethanol | 26.4 | ethanol | 26.32 |
| Tween 80 | 58.6 | Tween 80 | 58.71 |
| water | 0 | water | 0 |
| glycerol | 0 | glycerol | 0 |
| lutein ester | 0.19 | free lutein | 0.36 |

| D.2: 30% aqueous phase (W/O microemulsion) | | | |
|---|---|---|---|
| Component | Concentration(%) | Component | Concentration(%) |
| D-limonene | 9.06 | R(+)-limonene | 9.22 |
| ethanol | 18.13 | ethanol | 18.44 |
| Tween 80 | 40.99 | Tween 80 | 41.67 |
| water | 22.97 | water | 22.37 |
| glycerol | 7.65 | glycerol | 7.45 |
| lutein ester | 0.16 | freelutein | 0.167 |

| D.3: 70% aqueous phase (O/W microemulsion) | | | |
|---|---|---|---|
| Component | Concentration(%) | Component | Concentration(%) |
| D-limonene | 4.1 | R(+)-limonene | 3.99 |
| ethanol | 8.21 | ethanol | 7.99 |
| Tween 80 | 18.07 | Tween 80 | 18.23 |
| water | 51.94 | water | 52.28 |
| glycerol | 17.31 | glycerol | 17.42 |
| lutein ester | 0.0.47 | free lutein | 0.0126 |

D.4: Free Lutein in a 70% Aqueous Phase (O/W Nano-Sized Structures)

| Component | Concentration (%) |
|---|---|
| D-limonene | 1.72 |
| ethanol | 13.79 |
| castor oil EO40 | 15.1 |
| water | 52.53 |
| glycerol | 17.51 |
| free lutein | 0.006 |

The nanosized structured liquid concentrates can also comprise ratios of other than 1:1 for the water/PG or ethanol/solvent {R(+)-limonene}. The following examples exhibit such systems containing lycopene, phytosterol, lutein ester and free lutein.

| E. Lycopene solubilization in a ethanol:solvent ratio of 2:1 70% aqueous phase (O/W) | |
|---|---|
| Component | Concentration (%) |
| [1]lycopene | 0.02 |
| R(+)-limonene | 3.98 |
| ethanol | 7.97 |
| Tween 60 | 17.94 |
| PG | 34.88 |
| water | 34.88 |

[1]Oleoresin containing 6% lycopene.

| F. Phytosterol solubilization in a water:PG ratio of 1:2 70% aqueous phase (O/W) | |
|---|---|
| Component | Concentration (%) |
| phytosterol | 1.0 |
| R(+)-limonene | 5.94 |
| ethanol | 5.94 |
| Tween 60 | 17.82 |
| PG | 46.2 |
| water | 23.1 |

| G. 70% aqueous phase (O/W nano-sized structures) of lutein ester in a solvent:ethanol ratio of 1:3 | |
|---|---|
| Component | Concentration (%) |
| D-limonene | 3.08 |
| ethanol | 9.23 |
| Tween 80 | 18.07 |
| water | 51.94 |
| glycerol | 17.31 |
| lutein ester | 0.047 |

| H. 70% aqueous phase (O/W nano-sized structures) of lutein ester in a solvent:ethanol ratio of 1:4 | |
|---|---|
| Component | Concentration (%) |
| D-limonene | 2.46 |
| ethanol | 9.85 |
| Tween80 | 18.07 |
| water | 51.94 |
| glycerol | 17.31 |
| lutein ester | 0.047 |

The invention claimed is:
1. Structured liquid concentrates of self-assembled nano-sized emulsions, comprising:
   (i) an aqueous phase comprising water and at least one co-surfactant selected from $C_{2-16}$-alcohols;
   (ii) a polyol co-solvent selected from the group consisting of alcohols, polyalcohols, aldehydes, ketones, thiols, mono- and -di-saccharides;
   at least one surfactant of hydrophilic nature; and
   (iii) an oil phase comprising at least one solvent selected from the group consisting of long chain fatty alcohols

$C_{5-18}$, $C_{2-12}$-ketone, $C_{2-12}$-aldehyde, $C_{2-24}$-fatty acid or their esters, glycerol mono, di and tri-esters, terpene, terpin, terpinene, limonene, penta- or tetracyclic triterpenic alcohols, sterol, alkylsterol, essential oil oleoresins, fat soluble lipidic vitamins, fennel oil, ginger oil, lavender oil, eucalyptus oil, anise oil, lemon oil, mandarin oil, peppermint oil, oregano oil, lime oil, tangerine oil, spearmint oil, triethyl citrate, ethyl oleate, ethyl caprylate, anisole, anisyl alcohol, benzyl acetate, benzyl alcohol, benzyl propionate, ethyl lactate, phenethyl alcohol, terpenes and camphors selected from α-pinene, borneol, camphour, cineole, carvone, terpineol, menthol, menthone, thymol, geraniol, citral, terpinolene, hemonene, citronellal, natural flavoring materials selected from linalool, eugenol, vanillin, synthetic flavoring materials selected from hexyl alcohol, hexyl aldehyde, benzaldehyde, cinnamic aldehyde, citronellyl butyrate, nerol, phelandrene, phenyl ethyl acetate, ethyl propionate, ethyl laurate, ethyl decanoate, ethyl butyrate, ethyl hexanoate, ethyl caprylate, brandy flavoring oil, apple flavoring oil, paprica flavoring oil, blackberry flavoring oil, blueberry flavoring oil, honey flavoring oil, licorice flavoring oil, maple flavoring oil, strawberry flavoring oil, watermelon flavoring oil, wherein said solvent may further comprise at least one co-solvent selected from fatty acids, fatty alcohols, sterols, terpins, terpenines, essential oils, vitamins, wherein upon assembly, said emulsion forming a structure, the structure within the self-assembled structured liquid concentrates is maintained when said concentrate is diluted in a water or oil-based medium to any desired dilution.

2. Concentrates according to claim 1, wherein said at least one surfactant is food grade surfactant and is selected from the group consisting of ethoxylated castor oil, ethoxylated sorbitan esters selected from ethoxylated sorbitan -monostearate, -monooleate, monolaurate, sucrose esters, polyglycerol esters selected from mono, di, tri, tetra up to deca glycerol, esters of lauric ($C_{12}$); myristic ($C_{14}$); palmitic ($C_{16}$); stearic ($C_{18}$); oleic ($C_{18:1}$); linoleic ($C_{18:2}$) acids, combinations of fatty acids and ethoxylated mono-diglycerides, or mixtures thereof.

3. Concentrates according to claim 1, wherein the polyol co-solvent is selected from the group of aldo- or keto-sugars, oligomeric carbohydrates or a polyalcohol.

4. Concentrates according to claim 1, wherein said solvent is selected from the group consisting of limonene, tocopherol, tocopherol-acetate or triacetin.

5. Concentrates according to claim 1, where the ratio between the surfactant phase and oil phase is 3:2.

6. Structured liquid concentrates of self-assembled nano-sized emulsions, comprising:
   (i) water;
   (ii) a polyol co-solvent selected from the group consisting of alcohols, polyalcohols, aldehydes, ketones, thiols, mono- and -di-saccharides;
   (iii) at least one surfactant of hydrophilic nature;
   (iv) at least one co-surfactant selected from $C_{2-16}$-alcohols; and
   (v) an oil phase comprising at least one solvent selected from the group consisting of long chain fatty alcohols $C_{5-18}$,-ketone, $C_{2-12}$-aldehyde, $C_{2-24}$-fatty acid or their esters, glycerol mono, di and tri-esters, terpene, terpin, terpinene, limonene, penta- or tetracyclic triterpenic alcohols, sterol, alkylsterol, essential oil oleoresins, fat soluble lipidic vitamins, fennel oil, ginger oil, lavender oil, eucalyptus oil, anise oil, lemon oil, mandarin oil, peppermint oil, oregano oil, lime oil, tangerine oil, spearmint oil, triethyl citrate, ethyl oleate, ethyl caprylate, anisole, anisyl alcohol, benzyl acetate, benzyl alcohol, benzyl propionate, ethyl lactate, phenethyl alcohol, terpenes and camphors selected from α-pinene, borneol, camphour, cineole, carvone, terpineol, menthol, menthone, thymol, geraniol, citral, terpinolene, hemonene, citronellal, natural flavoring materials selected from linalool, eugenol, vanillin, synthetic flavoring materials selected from hexyl alcohol, hexyl aldehyde, benzaldehyde, cinnamic aldehyde, citronellyl butyrate, nerol, phelandrene, phenyl ethyl acetate, ethyl propionate, ethyl laurate, ethyl decanoate, ethyl butyrate, ethyl hexanoate, ethyl caprylate, brandy flavoring oil, apple flavoring oil, paprica flavoring oil, blackberry flavoring oil, blueberry flavoring oil, honey flavoring oil, licorice flavoring oil, maple flavoring oil, strawberry flavoring oil, watermelon flavoring oil, wherein said solvent may further comprise at least one co-solvent selected from fatty acids, fatty alcohols, sterols, terpins, terpenines, essential oils, vitamins, wherein upon assembly, said emulsion forming a structure, the structure within the self-assembled structured liquid concentrates is maintained when said concentrate is diluted in a water or oil-based medium, further comprising:
   oil soluble, oil non-soluble or water soluble material selected from the group consisting of nutraceuticals, food supplements, food additives, plant extracts, medicaments, peptides, proteins or carbohydrates, wherein the oil soluble, oil non-soluble, or water soluble material is solubilized in the oil phase or aqueous phase.

7. Concentrates according to claim 6, wherein said at least one surfactant is food grade and is selected from the group consisting of ethoxylated castor oil, ethoxylated sorbitan esters selected from ethoxylated sorbitan -monostearate, -monooleate, monolaurate, sucrose esters, polyglycerol esters selected from mono, di, tri, tetra up to deca glycerol, esters of launch ($C_{12}$); myristic ($C_{14}$); palmitic ($C_{16}$); stearic ($C_{18}$); oleic ($C_{18:1}$); linoleic ($C_{18:2}$) acids, combinations of fatty acids and ethoxylated mono-diglycerides, or mixtures thereof.

8. Nano-sized self-assembled structured liquid concentrates according to claim 6, wherein the polyol co-solvent is selected from the group of aldo- or keto-sugars, oligomeric carbohydrates.

9. Concentrates according to claim 6, wherein said solvent is selected from the group consisting of limonene, tocopherol, tocopherol-acetate or triacetin.

10. Concentrates according to claim 6, wherein said oil soluble, oil non-soluble or water soluble material is a nutraceutical selected from the group comprising lutein, lutein esters, β-carotene, lycopene, $Co-Q_{10}$, flax seed oil, lipoic acid, vitamin $B_{12}$, vitamin D, α-and γ-polyunsaturated fatty acids or phytosterols.

11. Concentrates according to claim 6 in the form of aqueous continuous phase comprising (wt/wt) 0.1 to 40% oil phase, 0.01–40% solubilized matter selected from oil-soluble, oil non-soluble or water-soluble nutraceuticals, food supplements, food additives, plant extracts, medicaments, peptides, proteins or carbohydrates and 40–99.8% water-soluble matter.

12. Concentrates according to claim 6 in the form of oil continuous phase comprising (wt/wt) 0.01–40% water-soluble phase, 0.01–40% solubilized matter selected from oil-soluble, oil non-soluble or water-soluble nutraceuticals, food supplements, food additives, plant extracts, medicaments, peptides, proteins or carbohydrates and 40–99.8% oil soluble matter.

13. Concentrates according to claim 6 in the form of bicontinuous phase comprising (wt/wt) 20–60% oil soluble phase, 0.01–60% solubilized matter selected from oil-soluble, oil non-soluble or water-soluble nutraceuticals, food supplements, food additives, plant extracts, medicaments, peptides, proteins or carbohydrates and 20–60% water soluble matter.

14. Food product, medicament, or cosmetic preparation comprising concentrates in the form of an aqueous continuous phase according to claim 11.

15. Food product, medicament, or cosmetic preparation comprising concentrates in the form of oil continuous phase according to claim 12.

16. Food product, medicament, or cosmetic preparation comprising concentrates in the form of a bi continuous phase according to claim 13.

17. Concentrates in the form of an aqueous continuous phase according to claim 11 for use in enhancing bioavailability of said oil-soluble, oil non-soluble or water-soluble nutraceuticals, food supplements, food additives, plant extracts, medicaments, peptides, proteins or carbohydrates.

18. Concentrates in the form of an oil continuous phase according to claim 12 for use in enhancing bioavailability of said oil-soluble, oil non-soluble or water-soluble nutraceuticals, food supplements, food additives, plant extracts, medicaments, peptides, proteins or carbohydrates.

19. Concentrates in the form of an bicontinuous phase according to claim 13 for use in enhancing bioavailability of said oil-soluble, oil non-soluble or water-soluble nutraceuticals, food supplements, food additives, plant extracts, medicaments, peptides, proteins or carbohydrates.

20. Structured liquid concentrates of self-assembled nano-sized emulsions, comprising:
   (i) water;
   (ii) a polyol co-solvent selected from the group consisting of alcohols, polyalcohols, aldehydes, ketones, thiols, mono- and di-saccharides;
   (iii) at least one surfactant of hydrophilic nature;
   (iv) at least one co-surfactant selected from $C_{2-16}$-alcohols;
   (v) an oil phase comprising at least one solvent selected from the group consisting of long chain fatty alcohols $C_{5-18}$, $C_{2-12}$-ketone, $C_{2-12}$-aldehyde, $C_{2-24}$-fatty acid or their esters, glycerol mono, di and TN-esters, terpene, terpin, terpinene, limonene, penta- or -tetracyclic triterpenic alcohols, sterol, alkylsterol, essential oil oleoresins, fat soluble lipidic vitamins, fennel oil, ginger oil, lavender oil, eucalyptus oil, anise oil, lemon oil, mandarin oil, peppermint oil, oregano oil, lime oil, tangerine oil, spearmint oil, triethyl citrate, ethyl oleate, ethyl caprylate, anisole, anisyl alcohol, benzyl acetate, benzyl alcohol, benzyl propionate, ethyl lactate, phenethyl alcohol, terpenes and camphors selected from α-pinene, bowel, camphour, cineole, carvone, terpineol, menthol, menthone, thymol, geraniol, citral, terpinolene, hemonene, citronellal, natural flavoring materials selected from linalool, eugenol, vanillin, synthetic flavoring materials selected from hexyl alcohol, hexyl aldehyde, benzaldehyde, cinnamic aldehyde, citronellyl butyrate, nerol, phelandrene, phenyl ethyl acetate, ethyl propionate, ethyl laurate, ethyl decanoate, ethyl butyrate, ethyl hexanoate, ethyl caprylate, brandy flavoring oil, apple flavoring oil, paprika flavoring oil, blackberry flavoring oil, blueberry flavoring oil, honey flavoring oil, licorice flavoring oil, maple flavoring oil, strawberry flavoring oil, watermelon flavoring oil, wherein said solvent may further comprise at least one co-solvent selected from fatty acids, fatty alcohols, sterols, terpins, terpenines, essential oils, vitamins, oil soluble, oil non-soluble or water soluble material selected from the group consisting of nutraceuticals, food supplements, food additives, plant extracts, medicaments, peptides, proteins or carbohydrates, wherein upon assembly, said emulsion forming a structure, the structure within the self-assembled structured liquid concentrates being maintained when said concentrate is diluted in a water or oil based medium, said emulsion being in the form of one of the following:
(a) an aqueous continuous phase comprising (wt/wt) 0.1 to 40% oil phase, 0.01–40% solubilized matter selected from oil-soluble, oil non-soluble or water-soluble nutraceuticals, food supplements, food additives, plant extracts, medicaments, peptides, proteins or carbohydrates and 40–99.8% water-soluble matter;
(b) an oil continuous phase comprising (wt/wt) 0.01–40% water-soluble phase, 0.01–40% solubilized matter selected from oil-soluble, oil non-soluble or water-soluble nutraceuticals, food supplements, food additives, plant extracts, medicaments, peptides, proteins or carbohydrates and 40–99.8% oil soluble matter; or
(c) a bicontinuous phase bicontinuous phase comprising (wt/wt) 20–60% oil soluble phase, 0.01–60% solubilized matter selected from oil-soluble, oil non-soluble or water-soluble nutraceuticals, food supplements, food additives, plant extracts, medicaments, peptides, proteins or carbohydrates and 20–60% water soluble matter.

* * * * *